United States Patent [19]

Paul

[11] Patent Number: 4,459,403
[45] Date of Patent: Jul. 10, 1984

[54] 5-SUBSTITUTED AMINO-6H-1,2,4-OXADIAZIN-3-(2H)-ONES

[75] Inventor: Albertha M. Paul, Holliston, Mass.

[73] Assignee: The Dow Chemical Company, Midland, Mich.

[21] Appl. No.: 450,715

[22] Filed: Dec. 17, 1982

[51] Int. Cl.$^3$ ............................................ C07D 273/04
[52] U.S. Cl. ............................................... 544/68; 71/92
[58] Field of Search ............................ 544/68; 542/420

[56] References Cited

U.S. PATENT DOCUMENTS 3,238,200  3/1966  Bernstein et al. .................... 260/244
3,600,386  8/1971  Levitt ................................. 260/244

OTHER PUBLICATIONS

Berkowitz, *J. Org. Chem.*, 41 (19), 3128, (1976).
Berkowitz, *J. of Med. Chem.*, 20 (1), 134, (1977).
Bennouna et al., *J. of Heterocyclic Chemistry*, 16, 161–167, (1979).

*Primary Examiner*—Richard Raymond
*Attorney, Agent, or Firm*—Norman L. Sims

[57] ABSTRACT

This invention relates to novel 5-substituted amino-6H-1,2,4-oxadiazin-3(2H)-ones wherein the 5-amino group is N-substituted with a $C_{4-20}$ alkyl or alkenyl group, a phenyl group with an amide, alkoxy or alkyl ester in the meta or para position, a pyridinyl group substituted with one or two alkyl groups, a 3,4,5-trialkoxyphenylmethylene group, or the nitrogen attached to the 5 carbon is part of a heterocyclic ring wherein the heterocyclic ring is imidazole, imidazolidinedione, imidazolidinyl, morpholinyl, piperazinyl or pyrrolidinyl.

6 Claims, No Drawings

5-SUBSTITUTED AMINO-6H-1,2,4-OXADIAZIN-3-(2H)-ONES

BACKGROUND OF THE INVENTION

This invention relates to 6H-1,2,4-oxadiazin-3(2H)-ones.

Berkowitz et al., "Synthesis and Antimicrobial Activity of Certain 6H-1,2,4-Oxadiazin-3(2H)-ones", *Journal of Medicinal Chemistry*, 20(1), 134 (1977), disclose 6H-1,2,4-oxadiazin-3(2H)-ones of the formula

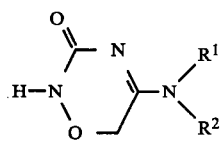

wherein $R^1$ is hydrogen or methyl and $R^2$ is hydrogen, methyl, hydroxy, amino, phenylmethylene or diphenylmethylene. The authors disclose that contacting 6H-1,2,4-oxadiazin-3(2H)-one-5(4H)-thione with hydroxylamine, hydrazine, methylamine or benzylamine procedure yields the N-substituted 5-amino-6H-1,2,4-oxadiazin-3(2H)-ones corresponding to the formula above. It is further taught that refluxing a dioxane solution of 6H-1,2,4-oxadiazin-3,5-(2H,4H)-dione with benzylamine or aminodiphenylmethane and hexamethyldisilazane in the presence of ammonium sulfate prepares 5-benzylamino-6H-1,2,4-oxadiazin-3(2H)-one and 5-diphenylmethylamino-6H-1,2,4-oxadiazin-3(2H)-one. These compounds demonstrated antimicrobial activity.

Berkowitz et al., "6-Oxa Analogues of Pyrimidines and Pyrimidine Nucleosides", *Journal of Organic Chemistry*, 41(19), 3128 (1976), disclose that the amination of 6H-1,2,4-oxadiazin-3(2H)-one-5(4H)-thione with ammonia and dimethylamine prepares 5-amino-6H-1,2,4-oxadiazin-3(2H)-one and 5-dimethylamino-6H-1,2,4-oxadiazin-3(2H)-one.

SUMMARY OF THE INVENTION

The invention is 5-substituted amino-6H-1,2,4-oxadiazin-3(2H)-ones of the formula

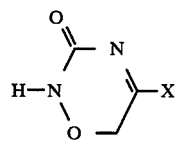

wherein X is an imidazole, imidazolidinedione, imidazolidinyl, morpholinyl, piperazinyl, or pyrrolidinyl group; or a group corresponding to the formula

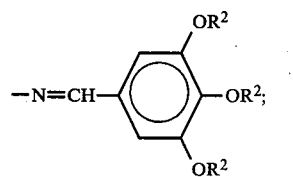

or a substituent corresponding to the formula —NHR$^1$ wherein R$^1$ is a C$_{4-20}$ alkyl group, C$_{4-20}$ alkenyl group,

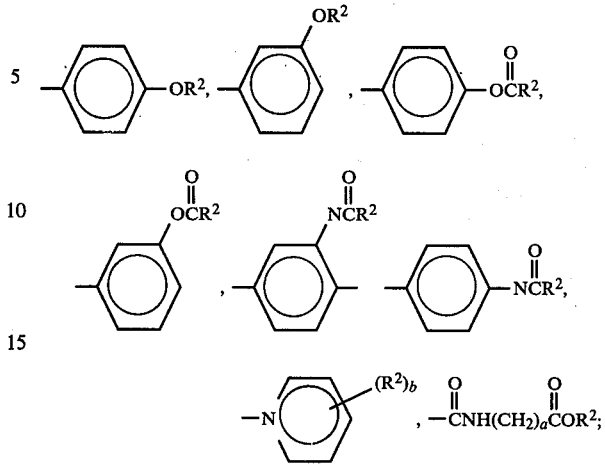

wherein $R^2$ is a $C_{1-3}$ lower alkyl group, a is an integer of from 1 to 5 inclusive, and b is an integer of 1 or 2.

These novel compounds are useful as herbicides with pre- and post-emergent activity against grassy and broadleaf species with unusual selectivity toward sugar beets.

DETAILED DESCRIPTION OF THE INVENTION

Preferred 5-substituted amino-6H-1,2,4-oxadiazin-3(2H)-ones include those represented by the formula

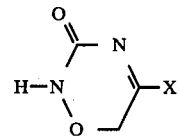

wherein X is an imidazole, imidazolidinedione, imidazolidinyl, morpholinyl, piperazinyl, pyrrolidinyl group; or a group corresponding to the formula

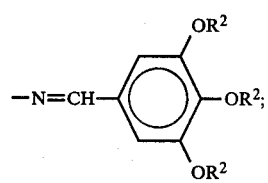

or a substituent of the formula NHR$^1$ wherein R$^1$ is

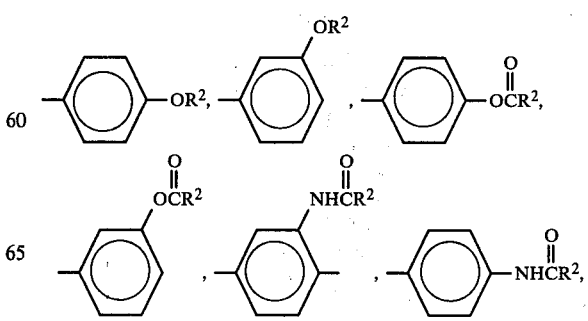

-continued

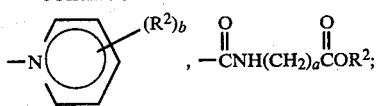

wherein $R^2$ is a $C_{1-3}$ lower alkyl group, a is an integer of from 1 to 5 inclusive, and b is an integer of 1 or 2.

$R^1$ is preferably

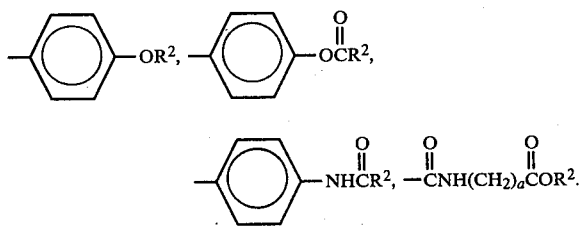

$R^2$ is preferably methyl and a is preferably 1.

Examples of compounds within the scope of this invention include: 5-dodecylamino-6H-1,2,4-oxadiazin-3(2H)-one; 5-decylamino-6H-1,2,4-oxadiazin-3(2H)-one; 5-octylamino-6H-1,2,4-oxadiazin-3(2H)-one; 5-butylamino-6H-1,2,4-oxadiazin-3(2H)-one; 5-(4-octadecenylamino)-6H-1,2,4-oxadiazin-3(2H)-one; 5-((4,6-dimethyl-2-pyridinyl)amino)-6H-1,2,4-oxadiazin-3(2H)-one; 4-((3,6-dihydro-3-oxo-2H-1,2,4-oxadiazin-5-yl)amino)benzoic acid, methyl ester; 5-((4-acetamidephenyl)amino)-6H-1,2,4-oxadiazin-3(2H)-one; 5-((4-methoxyphenyl)amino)-6H-1,2,4-oxadiazin-3(2H)-one; 5-(1H-imidazol-1-yl)-6H-1,2,4-oxadiazin-3(2H)-one; 1-(3,6-dihydro-3-oxo-2H-1,2,4-oxadiazin-5-yl)-2,4-imidazolidinedione; 5-(2-oxo-1-imidazolidinyl)-6H-1,2,4-oxadiazin-3(2H)-one; 5-(4-morpholinyl)-6H-1,2,4-oxadiazin-3(2H)-one; 5-(1-piperadinyl)-6H-1,2,4-oxadiazin-3(2H)-one; 5-(1-piperazinyl)-6H-1,2,4-oxadiazin-3(2H)-one; 5-(1-pyrrolidinyl)-6H-1,2,4-oxadiazin-3(2H)-one; 5-(((3,4,5-trimethoxyphenyl)methylene)amino)-6H-1,2,4-oxadiazin-3(2H)-one; or N-(3,6-dihydro-3-oxo-2H-1,2,4-oxadiazin-5-yl)aminocarbonyl-glycine, ethyl ester. Examples of preferred compounds within the scope of this invention include: 5-(4-octadecenylamino)-6H-1,2,4-oxadiazin-3(2H)-one; 5-((4,6-dimethyl-2-pyridinyl)amino)-6H-1,2,4-oxadiazin-3(2H)-one; 4-((3,6-dihydro-3-oxo-2H-1,2,4-oxadiazin-5-yl)amino)benzoic acid, methyl ester; 5-((4-acetamidophenyl)amino)-6H-1,2,4-oxadiazin-3(2H)-one; 5-((4-methoxyphenyl)amino)-6H-1,2,4-oxadiazin-3(2H)-one; 5-(1H-imidazol-1-yl)-6H-1,2,4-oxadiazin-3(2H)-one; 1-(3,6-dihydro-3-oxo-2H-1,2,4-oxadiazin-5-yl)-2,4-imidazolidinedione; 5-(2-oxo-1-imidazolidinyl)-6H-1,2,4-oxadiazin-3(2H)-one; 5-(4-morpholinyl)-6H-1,2,4-oxadiazin-3(2H)-one; 5-(1-piperadinyl)-6H-1,2,4-oxadiazin-3(2H)-one; 5-(1-piperazinyl)-6H-1,2,4-oxadiazin-3(2H)-one; 5-(1-pyrrolidinyl)-6H-1,2,4-oxadiazin-3(2H)-one; 5-(((3,4,5-trimethoxyphenyl)methylene)amino)-6H-1,2,4-oxadiazin-3(2H)-one; or N-(3,6-dihydro-3-oxo-2H-1,2,4-oxadiazin-5-yl)aminocarbonyl-glycine, ethyl ester.

The novel compounds of this invention are preferably prepared by one of two methods. In one method, one molar equivalent of 6H-1,2,4-oxadiazin-3,5(2H,4H)-dione is contacted with at least 1.2 molar equivalents of a suitable amine, corresponding to the formula X-H, wherein X is as defined above, in a dioxane and hexamethyldisilazane solvent in the presence of about $3.7 \times 10^{-4}$ equivalents of ammonium sulfate. This mixture is then refluxed for between about 1 to 17 hours. After cooling, the dioxane and hexamethyldisilazane are removed in vacuo, and the residue is dried in a vacuum oven for about two hours. The dried residue is then washed with petroleum ether and recovered by filtration.

The second method of preparation comprises contacting one molar equivalent of 6H-1,2,4-oxadiazin-3(2H)-one-5(4H)-thione with at least one molar equivalent of a suitable amine as defined above, in dioxane at ambient temperature and pressure. The reaction time can be between about 15 minutes to 17 hours depending upon the reactivity (nucleophilicity) of the amine. The product is removed from the reaction mixture by filtration and washed with chloroform and ether.

The 1,2,4-oxadiazinediones which are used as starting materials in this invention can be prepared by the process described in Bernstein et al., U.S. Pat. No. 3,238,200 (incorporated herein by reference).

The 6H-1,2,4-oxadiazin-3(2H)-one-5(4H)-thione used to prepare the novel compounds of this invention is prepared by refluxing 6H-1,2,4-oxadiazin-3,5(2H,4H)-dione with phosphorus pentasulfide in anhydrous dioxane.

The novel compounds of this invention have demonstrated herbicidal activity against broadleaf crops and weeds, and grassy crops and weeds in both pre-emergent and post-emergent applications. They have shown a selectivity for sugar beets. These compounds demonstrate antimicrobial activity against several bacteria and fungi. It has been shown that 6H-1,2,4-oxadiazin-3(2H)-ones can be used as urinary tract anti-infectives.

SPECIFIC EMBODIMENTS

The following examples are included to illustrate the invention are not intended to limit the scope of the invention or the claims.

EXAMPLE 1

5-((4,6-Dimethyl-2-pyridinyl)amino)-6H-1,2,4-oxadiazin-3(2H)-one

To 0.5 g (0.0043 mole) of 6H-1,2,4-oxadiazin-3(2H)-one-5(4H)-thione dissolved in 10 ml of freshly distilled dry dioxane is added 0.56 g (0.0043 mole) of 2-amino-4,6-dimethyl pyridine. The reaction mixture is stirred at room temperature for 17 hours and the dioxane removed on a rotovap. The crystalline material is washed with chloroform, then with ether to give 0.65 g (69 percent) of 5-((4,6-dimethyl-2-pyridinyl)amino)-6H-1,2,4-oxadiazin-3(2H)-one.

EXAMPLE 2

5-Dodecylamino-6H-1,2,4-oxadiazin-3(2H)-one

A solution of 1.16 g (0.010 mole) of 6H-1,2,4-oxadiazin-3,5(2H,4H)-dione, 5 mg of ammonium sulfate, 2.22 g (0.012 mole) of dodecylamine and 20 ml of hexamethyldisilazane in 40 ml of freshly distilled dry dioxane is refluxed for 17 hours. After cooling, the dioxane and hexamethyldisilazane are removed in vacuo and the syrupy residue is dried on a vacuum pump for 2 hours. The resulting semi-solid residue is triturated with 100 ml of petroleum ether and filtered to yield 2.5 g (88 percent) of 5-dodecylamino-6H-1,2,4-oxadiazin-3(2H)-one.

EXAMPLE 3

5-Decylamino-6H-1,2,4-oxadiazin-3(2H)-one

A solution of 5.0 g (0.043 mole) of 6H-1,2,4-oxadiazin-3,5(2H,4H)-dione, 0.025 g of ammonium sulfate, 35 ml of hexamethyldisilazane and 19.5 g (0.123 mole) of n-decylamine in 200 ml freshly distilled dry dioxane is refluxed for 17 hours. After cooling, the dioxane and hexamethyldisilazane are removed in vacuo and the syrupy residue is dried on a vacuum pump for 2 hours. The resulting semi-solid residue is triturated with 100 ml of petroleum ether and filtered to yield approximately 10 g (92 percent) of 5-decylamino-6H-1,2,4-oxadiazin-3(2H)-one.

EXAMPLE 4

5-Octylamino-6H-1,2,4-oxadiazin-3(2H)-one

A solution of 1.16 g (0.010 mole) of 6H-1,2,4-oxadiazin-3,5(2H,4H)-dione, 5 mg of ammonium sulfate, 1.55 g (0.012 mole) of n-octylamine and 20 ml hexamethyldisilazane in 40 ml freshly distilled dry dioxane is refluxed for 17 hours. After cooling to room temperature, the dioxane and hexamethyldisilazane are removed in vacuo and the syrupy residue is dried on a vacuum pump for 2 hours. The resulting semi-solid residue is triturated with 100 ml of petroleum ether and filtered to yield 0.85 g (37 percent) of 5-octylamino-6H-1,2,4-oxadiazin-3(2H)-one.

EXAMPLE 5

5-Butylamino-6H-1,2,4-oxadiazin-3(2H)-one

A solution of 1.16 g (0.010 mole) of 6H-1,2,4-oxadiazin-3,5(2H,4H)-dione, 5 mg of ammonium sulfate, 0.88 g (0.012 mole) of n-butylamine and 20 ml hexamethyldisilazane in 40 ml freshly distilled dry dioxane is refluxed for 17 hours. After cooling to room temperature, the dioxane and hexamethyldisilazane are removed in vacuo and the syrupy residue is dried on a vacuum pump for 2 hours. The resulting semi-solid residue is triturated with 100 ml of petroleum ether and filtered to yield 1.02 g (87 percent) of 5-butylamino-6H-1,2,4-oxadiazin-3(2H)-one.

EXAMPLE 6

5-(4-Octadecenylamino)-6H-1,2,4-oxadiazin-3(2H)-one

To 0.66 g (0.005 mole) of 6H-1,2,4-oxadiazin-3(2H)-one-5(4H)-thione dissolved in 10 ml of freshly distilled dry dioxane is added 1.33 g (0.0051 mole) of oleylamine. The reaction mixture is stirred for 17 hours at room temperature and the crystalline material filtered, washed with additional dry dioxane and chloroform, and dried to give 0.3 g (16 percent) of 5-(4-octadecenylamino)-6H-1,2,4-oxadiazin-3(2H)-one.

EXAMPLE 7

4-((3,6-Dihydro-3-oxo-2H-1,2,4-oxadiazin-5-yl)amino)-benzoic acid, methyl ester

A solution of 1.16 g (0.010 mole) of 6H-1,2,4-oxadiazin-3,5(2H,4H)-dione, 5 mg ammonium sulfate, 1.80 g (0.012 mole) of p-amino-methylbenzoate and 20 ml hexamethyldisilazane in 40 ml freshly distilled dry dioxane is refluxed for 17 hours. After cooling, the dioxane and hexamethyldisilazane are removed in vacuo and the syrupy residue is dried on a vacuum pump for 2 hours. The resulting semi-solid residue is triturated with 100 ml of petroleum ether and filtered to yield 1.56 g (63 percent) of 4-((3,6-dihydro-3-oxo-2H-1,2,4-oxadiazin-5-yl)amino)benzoic acid, methyl ester.

EXAMPLE 8

5-((4-Acetamidophenyl)amino)-6H-1,2,4-oxadiazin-3(2H)-one

A solution of 1.16 g (0.010 mole) of 6H-1,2,4-oxadiazin-3,5(2H,4H)-dione, 5 mg ammonium sulfate, 1.81 g (0.012 mole) of p-acetamidoaniline and 20 ml hexamethyldisilazane in 40 ml of freshly distilled dry dioxane is refluxed for 17 hours. After cooling, the dioxane and hexamethyldisilazane are removed in vacuo and the syrupy residue is dried on a vacuum pump for 2 hours. The resulting semi-solid residue is triturated with 100 ml of petroleum ether and filtered to yield 1.0 g (40 percent) of 5-((4-acetamidephenyl)amino)-6H-1,2,4-oxadiazin-3(2H)-one.

EXAMPLE 9

5-((4-Methoxyphenyl)amino)-6H-1,2,4-oxadiazin-3(2H)-one

A solution of 1.16 g (0.010 mole) of 6H-1,2,4-oxadiazin-3,5(2H,4H)-dione, 5 mg ammonium sulfate, 1.47 g (0.012 mole) of p-methoxyaniline and 20 ml hexamethyldisilazane in 40 ml of freshly distilled dry dioxane is refluxed for 17 hours. After cooling, the dioxane and hexamethyldisilazane are removed in vacuo and the syrupy residue is dried on a vacuum pump for 2 hours. The resulting semi-solid residue is triturated with 100 ml of petroleum ether and filtered to give a yield of 1.3 g (59 percent) of 5-((4-methoxyphenyl)amino)-6H-1,2,4-oxadiazin-3(2H)-one.

EXAMPLE 10

5-(1H-Imidazole-1-yl)-6H-1,2,4-oxadiazin-3(2H)-one

To a solution of 1.0 g (0.0075 mole) of 6H-1,2,4-oxadiazin-3(2H)-one-5(4H)-thione in 50 ml of freshly distilled dry dioxane is added 0.52 g (0.0077 mole) of imidazole. After stirring at room temperature for 17 hours, the solution is filtered, washed with chloroform and dried to give a yield of 0.7 g (56 percent) of 5-(1H-imidazol-1-yl)-6H-1,2,4-oxadiazin-3(2H)-one.

EXAMPLE 11

1-(3,6-Dihydro-3-oxo-2H-1,2,4-oxadiazin-5-yl)-2,4-imidazolidinedione

To a solution of 1.0 g (0.0075 mole) of 6H-1,2,4-oxadiazin-3(2H)-one-5(4H)-thione in 50 ml of freshly distilled dry dioxane is added 0.77 g (0.0077 mole) of hydantoin. After stirring at room temperature for 17 hours, the solution is filtered, washed with chloroform and dried to give a yield of 0.6 g (41 percent) of 1-(3,6-dihydro-3-oxo-2H-1,2,4-oxadiazin-5-yl)-2,4-imidazolidinedione.

EXAMPLE 12

5-(2-oxo-1-Imidazolidinyl)-6H-1,2,4-oxadiazin-3(2H)-one

To a solution of 1.0 g (0.0075 mole) of 6H-1,2,4-oxadiazin-3(2H)-one-5(4H)-thione in 50 ml of dry freshly distilled dioxane is added 0.66 g (0.007 mole) of 2-imidazolidone. After stirring at room temperature for 17 hours, the solution is filtered, washed with chloroform and dried to give a yield of 1.3 g (94 percent) of 5-(2-oxo-1-imidazolidinyl)-6H-1,2,4-oxadiazin-3(2H)-one.

EXAMPLE 13

5-(4-Morpholinyl)-6H-1,2,4-oxadiazin-3(2H)-one

To a solution of 0.5 g (0.0037 mole) of 6H-1,2,4-oxadiazin-3(2H)-one-5(4H)-thione dissolved in 10 ml of dry freshly distilled dioxane is added 0.34 g (0.0039 mole) of morpholine. After stirring at room temperature for 17 hours, the solution is filtered, washed with chloroform and dried to give a yield of 0.5 g (74 percent) of 5-(4-morpholinyl)-6H-1,2,4-oxadiazin-3(2H)-one.

EXAMPLE 14

5-(1-Piperidinyl)-6H-1,2,4-oxadiazin-3(2H)-one

To a solution of 0.7 g (0.005 mole) of 6H-1,2,4-oxadiazin-3(2H)-one-5(4H)-thione in 10 ml of dry freshly distilled dioxane is added 0.44 g (0.0052 mole) of piperidine. After stirring for 17 hours at room temperature, the solution is filtered, washed with chloroform and dried to give a yield of 0.49 g (54 percent) of 5-(1-piperidinyl)-6H-1,2,4-oxadiazin-3(2H)-one.

EXAMPLE 15

5-(1-Piperazinyl)-6H-1,2,4-oxadiazin-3(2H)-one

A solution of 1.16 g (0.010 of 6H-1,2,4-oxadiazin-3,5-(2H,4H)-dione, 5 mg of ammonium sulfate, 2.49 g (0.029 mole) of piperazine and 20 ml of hexamethyldisilazane in 40 ml of dry freshly distilled dioxane is refluxed for 17 hours. After cooling, the dioxane and hexamethyldisilazane are removed in vacuo and the syrupy residue is dried on a vacuum pump for 2 hours. The resulting semi-solid residue is triturated with 100 ml of petroleum ether and filtered to yield 0.78 g (42 percent) of 5-(1-piperazinyl)-6H-1,2,4-oxadiazin-3(2H)-one.

EXAMPLE 16

5-(1-Pyrrolidinyl)-6H-1,2,4-oxadiazin-3(2H)-one

A solution of 1.16 g (0.010 mole) of 6H-1,2,4-oxadiazin-3,5(2H,4H)-dione, 5 mg of ammonium sulfate, 2.06 (0.029 mole) of pyrrolidine and 20 ml of hexamethyldisilazane in 40 ml of dry freshly distilled dioxane is refluxed for 17 hours. After cooling, the dioxane and hexamethyldisilazane are removed in vacuo and the syrupy residue is dried on a vacuum pump for 2 hours. The resulting semi-solid residue is triturated with 100 ml of petroleum ether and filtered to yield 0.8 g (47 percent) of 5-(1-pyrrolidinyl)-6H-1,2,4-oxadiazin-3(2H)-one.

EXAMPLE 17

5-(((3,4,5-Trimethoxyphenyl)methylene)amino)-6H-1,2,4-oxadiazin-3(2H)-one

A solution of 1.0 g (0.0075 mole) of 5-amino-6H-1,2,4-oxadiazin-3(2H)-one, 1.5 g (0.0075 mole) of 3,4,5-trimethoxybenzaldehyde, 50 ml methanol and 3 ml of triethylamine is refluxed for 17 hours. After cooling, the methanol, water and triethylamine are removed on the rotovap and the remaining solvent removed on a vacuum pump. (Note: a negative 2,4-dinitrophenylhydrazone test was obtained.) A yield of 2.0 g (91.3 percent) of 5-(((3,4,5-trimethoxyphenyl)methylene)amino)-6H-1,2,4-oxadiazin-3(2H)-one is obtained.

EXAMPLE 18

N-(3,6-Dihydro-3-oxo-2H-1,2,4-oxadiazin-5-yl)aminocarbonyl-glycine, ether ester A solution of 1.0 g (0.0086 mole) of 5-amino-6H-1,2,4-oxadiazin-3(2H)-one and 1.0 g (0.0086 mole) of ethyl isocyanatoacetate in methanol is combined with cooling and stirring to give the desired product of N-(3,6-dihydro-3-oxo-2H-1,2,4-oxadiazin-5-yl)aminocarbonyl-glycine, ethyl ester which was isolated by filtration, followed by washing with ether and drying. A yield of 0.5 g (72 percent) is obtained.

What is claimed is:

1. 5-Substituted amino-6H-1,2,4-oxadiazin-3(2H)-ones of the formula

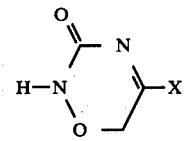

wherein X is an imidazole, imidazolidinedione, imidazolidinyl, morpholinyl, piperazinyl, or pyrrolidinyl group; or a group corresponding to the formula

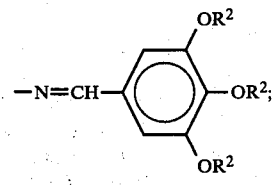

or a group corresponding to the formula $-NHR^1$ wherein $R^1$ is a $C_{4-20}$ alkenyl group,

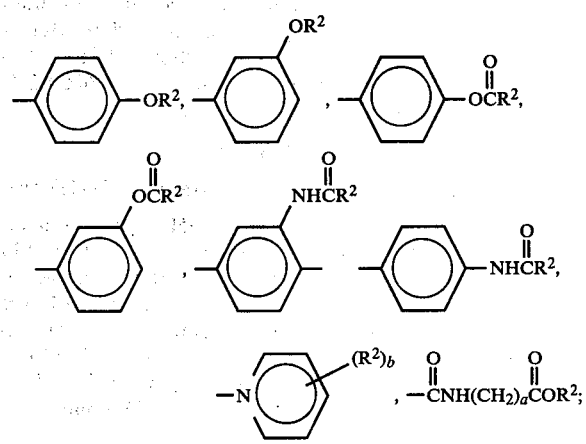

wherein $R^2$ is a $C_{1-3}$ lower alkyl group, a is an integer of from 1 to 5 inclusive, and b is an integer of 1 or 2.

2. 5-Substituted amino-6H-1,2,4-oxadiazin-3(2H)-ones of the formula

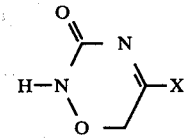

wherein X is an imidazole, imidazolidinedione, imidazolidinyl, morpholinyl, piperazinyl, pyrrolidinyl group or a substituent of the formula —NHR¹ wherein R¹ is

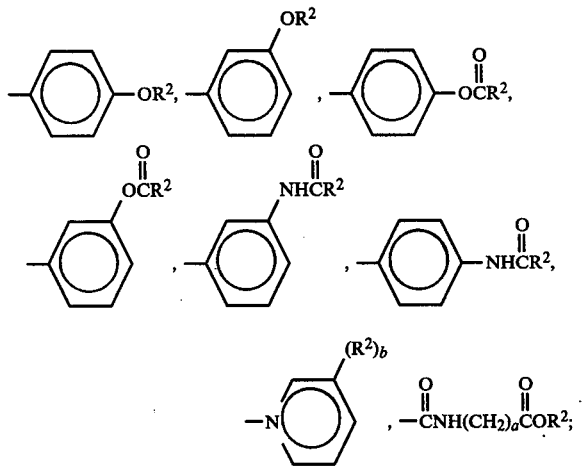

wherein $R^2$ is a $C_{1-3}$ lower alkyl group, a is an integer of from 1 to 5 inclusive, and b is an integer of 1 or 2.

3. The compounds of claim 2 wherein $R^2$ is methyl.

4. The compounds of claim 3 wherein a is 1.

5. The compounds according to claim 1 which are 5-(4-octadecenylamino)-6H-1,2,4-oxadiazin-3(2H)-one; 5-((4,6-dimethyl-2-pyridinyl)amino)-6H-1,2,4-oxadiazin-3(2H)-one; 4-((3,6-dihydro-3-oxo-2H-1,2,4-oxadiazin-5-yl)amino)benzoic acid; methyl ester; 5-((4-acetamidophenyl)amino)-6H-1,2,4-oxadiazin-3(2H)-one; 5-((4-methoxyphenyl)amino)-6H-1,2,4-oxadiazin-3(2H)-one; 5-(1H-imidazol-1-yl)-6H-1,2,4-oxadiazin-3(2H)-one; 1-(3,6-dihydro-3-oxo-2H-1,2,4-oxadiazin-5-yl)-2,4-imidazolidinedione; 5-(2-oxo-1-imidazolidinyl)-6H-1,2,4-oxadiazin-3(2H)-one; 5-(4-morpholinyl)-6H-1,2,4-oxadiazin-3(2H)-one; 5-(1-piperadinyl)-6H-1,2,4-oxadiazin-3(2H)-one; 5-(1-piperazinyl)-6H-1,2,4-oxadiazin-3(2H)-one; 5-(1-pyrrolidinyl)-6H-1,2,4-oxadiazin-3(2H)-one; 5-(((3,4,5-trimethoxyphenyl)methylene)amino)-6H-1,2,4-oxadiazin-3(2H)-one; or N-(3,6-dihydro-3-oxo-2H-1,2,4-oxadiazin-5-yl)aminocarbonyl-glycine, ethyl ester.

6. The compounds according to claim 2 which are 5-(4-octadecenylamino)-6-H-1,2,4-oxadiazin-3(2H)-one; 5-((4,6-dimethyl-2-pyridinyl)amino)-6H-1,2,4-oxadiazin-3(2H)-one; 4-((3,6-dihydro-3-oxo-2H-1,2,4-oxadiazin-5-yl)amino)benzoic acid, methyl ester; 5-((4-acetamidophenyl)amino)-6H-1,2,4-oxadiazin-3(2H)-one; 5-((4-methoxyphenyl)amino)-6H-1,2,4-oxadiazin-3(2H)-one; 5-(1H-imidazol-1-yl)-6H-1,2,4-oxadiazin-3(2H)-one; 1-(3,6-dihydro-3-oxo-2H-1,2,4-oxadiazin-5-yl)-2,4-imidazolidinedione; 5-(2-oxo-1-imidazolidinyl)-6H-1,2,4-oxadiazin-3(2H)-one; 5-(4-morpholinyl)-6H-1,2,4-oxadiazin-3(2H)-one; 5-(1-piperadinyl)-6H-1,2,4-oxadiazin-3(2H)-one; 5-(1-piperazinyl)-6H-1,2,4-oxadiazin-3(2H)-one; 5-(1-pyrrolidinyl)-6H-1,2,4-oxadiazin-3(2H)-one; 5-(((3,4,5-trimethoxyphenyl)methylene)amino)-6H-1,2,4-oxadiazin-3(2H)-one; or N-(3,6-dihydro-3-oxo-2H-1,2,4-oxadiazin-5-yl)aminocarbonyl-glycine, ethyl ester.

* * * * *